United States Patent [19]
Tomohisa et al.

[11] Patent Number: 5,798,120
[45] Date of Patent: Aug. 25, 1998

[54] ENTERIC GRANULE-CONTAINING TABLETS

[75] Inventors: Matsushita Tomohisa; Hashimoto Mitsuo, both of Tokyo, Japan

[73] Assignee: Tokyo Tanabe Company Limited, Tokyo, Japan

[21] Appl. No.: 624,510

[22] PCT Filed: Oct. 6, 1994

[86] PCT No.: PCT/JP94/01675

§ 371 Date: Apr. 5, 1996

§ 102(e) Date: Apr. 5, 1996

[87] PCT Pub. No.: WO95/10264

PCT Pub. Date: Apr. 20, 1995

[30] Foreign Application Priority Data

Oct. 12, 1993 [JP] Japan ................... 5-254049

[51] Int. Cl.$^6$ .................................. A61K 9/32
[52] U.S. Cl. .................... 424/482; 424/489; 424/474; 424/464; 424/461
[58] Field of Search .................. 424/482, 439, 424/464, 456, 474, 497, 468, 461

[56] References Cited

U.S. PATENT DOCUMENTS 4,874,614  10/1989  Becker ........................ 426/76

FOREIGN PATENT DOCUMENTS

| A 61-221115 | 10/1986 | Japan. |
| A-2-138210 | 5/1990 | Japan. |
| A 3-240724 | 10/1991 | Japan. |
| A-3-258730 | 11/1991 | Japan. |

Primary Examiner—Thurman K. Page
Assistant Examiner—William E. Benston, Jr.
Attorney, Agent, or Firm—Griffin, Butler, Whisenhunt & Szipl, LLP

[57] ABSTRACT

The present invention relates to enteric granule-containing tablets which are prepared by tabletting a mixture of enteric granules containing an active agent, with one or a combination of 2 or more compounds selected from synthetic hydrotalcite, dried aluminum hydroxide gel, aluminum hydroxide/sodium hydrogen carbonate coprecipitate, alumina hydroxide/magnesium, synthetic aluminum silicate and dihydroxyaluminumamino acetate. The invention provides high-strength tablets which are formulated with specific excipients which allow a higher enteric granule content, faster dispersion in the enteric granules, no loss of drug elution properties or acid resistance of the enteric granules upon tabletting, with less damage in the coating and low weight variation of the tablets during tabletting, as compared to tablets containing coated granules according to the prior art. This technique for achieving a high enteric granule content has additional merits including better versatility of dosages due to the small size of the tablets, and further applications for other drug agents.

16 Claims, 1 Drawing Sheet

ENTERIC GRANULE-CONTAINING TABLETS

This application is a 371 PCT/JP94/01675 filed Oct. 6, 1994.

FIELD OF THE INVENTION

The present invention relates to granule-containing tablets, also known as "multiple-unit tablets". More specifically, it relates to multiple-unit tablets whose units are enteric granules consisting of granules coated with an enteric coating.

BACKGROUND OF THE INVENTION

A common method of preparing enteric tablets involves forming an enteric coating on single-unit tablets. However, variations in body kinetics due mainly to elimination rates from the stomach have a large influence on the drug effects of the active agent, and this has highlighted the need for multiple-unit enteric tablets which exhibit satisfactorily reproducible absorption and undergo little variation due to body kinetics, etc.

The need for acid resistance of multiple-unit enteric tablets in the stomach is known, and yet deterioration of acid resistance by crushing of enteric granules during tablet preparation has been found to have an adverse effect on bioavailability. Furthermore, in order to prevent crushing of the enteric granules during tablet preparation, enteric granules are prepared by adding substances to the enteric coating which soften it, or the enteric granules are prepared as a solid dispersion of the drug in the enteric coating by some method, and an excipient is combined therewith for tabletting. Also, in order to prevent damage to the enteric coating, it becomes necessary to make the coating itself thicker, or combine a large amount of a specially processed excipient or the like to increase the size of the preparation itself (Japanese Unexamined Patent Publication Nos. 2-138210, 3-258730). Also, the mixing ratio of the enteric granules in the tablets is usually from 50% to a maximum of 70% with respect to the tablet weight. This results in relatively large tablets which are difficult to administer, and thus influences patient compliance. Tablets which are easy to administer normally have a size of from about 7 to 8 millimeters. Another problem is that differences in the particle size and specific gravity of the enteric granules and excipient cause variations in the mixing ratio due to unbalances during the mixing process, prior to tabletting, and during the tabletting.

SUMMARY OF THE INVENTION

In light of these circumstances, the present inventors have conducted diligent research with the object of obtaining enteric granule-containing tablets which have an adequate basic function, in terms of disintegration, dispersability and elution, and which are easy to administer. Other objects are that the enteric granules maintain acid resistance without undergoing damage when made into tablets and that the mixing ratio of the enteric granules has little variation. The above research has resulted in completion of the present invention based on the finding that compact tablets with satisfactory acid resistance and with a high proportion of granules may be produced by tabletting a mixture containing one or a combination of 2 or more compounds selected from the group consisting of synthetic hydrotalcite, dried aluminum hydroxide gel, aluminum hydroxide/sodium hydrogen carbonate coprecipitate, alumina hydroxide/magnesium, synthetic aluminum silicate and dihydroxyaluminumamino acetate (all of which are listed in the 12th Revision of Japanese Pharmacopoeia or the 1993 Japan Pharmacopoeia Medical Drug Standards), as an additive or additives with the enteric granules.

The mixture of the present invention has excellent moldability, exhibits sufficient hardness even at low amounts with low tabletting pressure, and allows a granule proportion of 75 to 90% by weight with respect to the total weight of the tablets. Since the mixing ratio includes additives which are mixed so as to coat the granules, there is little variation in the enteric granules prior to preparation of the tablets or during mixing, which thus ensures uniformity of the granules in the tablets.

The active agent according to the present invention is not particularly restricted, so long as it is an agent which is easily degraded by acids, or which is not properly released in the stomach as a result of drug stimulation, etc. Possible examples include benzimidazole-based antiulcer agents such as omeprazole, lanthoprazole or 2-(2-dimethylaminobenzyl)sulfinylbenzimidiazole; and other antiulcer drugs including proton pump inhibitors such as 5-methoxy-2-[[(4-methoxy-3,5-dimethyl-2-pyridyl) methyl] sulfinyl]imidazo[4,5-b]pyridine. The crude granules for the enteric coating are not particularly restricted so long as they are made by a common granulation method such as extrusion or tumbling granulation. The enteric coating used may be methacrylic acid copolymer LD, cellulose acetate phthalate, hydroxypropylmethyl cellulose phthalate or hydroxypropylmethyl cellulose acetate succinate (all of which are listed in the 12th Revision of Japanese Pharmacopoeia or the 1993 Medical Drug Standards).

The enteric granules are not particularly restricted so long as they are coated with an enteric coating using a fluidized-bed granulating/coating apparatus. Also, a plasticizer is preferably added during formulation of the coating to be coated on the granules, at 15–40 w/w %, and preferably 30–40 w/w % with respect to the total amount of the enteric coating. The plasticizer used may be polyethylene glycol (for example, Macrogol 4000 or Macrogol 6000, listed in the Japanese Pharmacopoeia, 12th Revision), triethyl citrate, or the like.

Production of the tablets of the invention may also include the use of an appropriate binder (hydroxypropyl cellulose, hydroxypropylmethyl cellulose, polyvinyl-pyrrolidone, etc.), disintegrator (crosslinked carboxy-methyl cellulose sodium, carboxymethyl cellulose calcium, etc.) or lubricant (talc, magnesium stearate, calcium stearate, etc.).

The tablets obtained according to the invention may also be coated for the purpose of masking or moisture resistance, as desired.

DESCRIPTION OF THE PREFERRED EMBODIMENT

Figure 1:
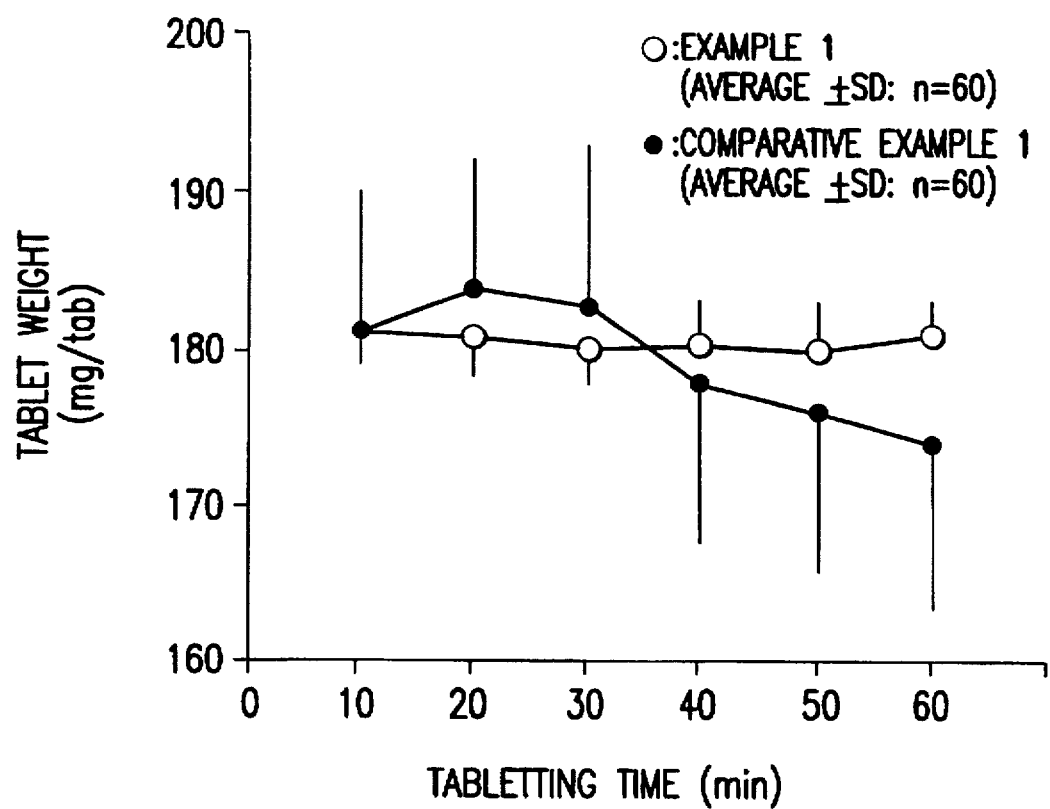
FIG. 1 is a graph showing the results of weight deviation testing for Example 1 and Comparative Example 1.

The present invention will now be explained by way of the following examples.

The methods of measuring the physical properties of the tablets in the examples and comparative examples are as follows.

Acid resistance (%): Expressed as the leakage of the active agent from the enteric granules in solution 1 (of the Japanese Pharmacopoeia). A lower value indicates greater stability in acids.

The rotating basket method (100 rpm) was employed using an elution tester (Model NTR-VS 3P, product of Toyama Sangyo, KK.). The test was conducted for 2 hours using solution 1 (of the Japanese Pharmacopoeia) as the test solution, and the average value of 3 repetitions was taken.

Disintegration time (min): Indicated as the time after administration required for the preparation to return from tablet form to granule form. A shorter time is preferred.

A disintegration tester (Model NT-4HS, product of Toyama Sangyo, KK.) was used, with solution 1 (of the Japanese Pharmacopoeia) as the test solution. The condition was observed noting the time for disintegration of the tablets and dispersion into granules. The average value of 6 repetitions was taken.

Elution time (min): The index was T75% (time required for effective component to elute to 75% of an indicated amount). A shorter time is preferred.

The rotating basket method (100 rpm) was employed using an elution tester (Model NTR-VS 3P, product of Toyama Sangyo, KK.). The test was conducted for 90 minutes using solution 2 (of the Japanese Pharmacopoeia) as the test solution, and comparison was made with the average T75% value from 3 repetitions.

Tablet hardness (Kp): A hardness of 3–4 Kp or greater is preferred since the tablets sometimes undergo further coating.

A load was applied to the tablets in the radial direction using a Schleuniger hardness meter, noting the load at which crumbling occurred. The average value of 10 repetitions was taken.

Abrasiveness test (no.): A smaller number of abraded tablets is preferred.

A count was made of the number of tablets exhibiting damage upon rotation of 20 tablet samples for 10 minutes in a tablet abrasiveness tester (product of Kayagaki Iatrophysics Industries, KK.).

Tablet weight variation: The tablets preferably have constant weight even over extended preparation.

The individual weights of 60 tablets were measured with an electron counter scale and the average and standard deviation were calculated.

EXAMPLE 1

A centrifugal fluid coating granulator (Model CF-360, product of Freund Indust., KK.) was used to coat 500 g of refined globular sucrose granules (32-42#) (Nonpareil, trademark of Freund Indust., KK.; hereunder referred to as "Nonpareil") with a mixture of 100 g 5-methoxy-2-[[4-methoxy-3,5-dimethyl-2-pyridyl)methyl]sulfinyl] imidazo [4,5-b]pyridine (hereunder referred to as "TU-199") and 500 g lactose (200#) (product of DMV Co.) while nebulizing 200 ml of a 3% aqueous solution of hydroxypropyl cellulose (product of Nihon Soda, KK., hereunder referred to as HPC-L), and this was followed by drying and sorting to obtain 1000 g of crude granules (20-42#). Using a fluidized-bed coating apparatus (FLOW COATER MINI, product of Freund Co.), the crude granules were coated with a mixed solution of 34 parts of the acrylic polymer-based coating agent, methacrylic acid copolymer-LD (product of Rome & Hearst, hereunder referred to as Eudragit L30D-55), 4 parts of Macrogol 6000 and 34 parts water, to 30% with respect to the crude granules, to prepare enteric granules. The elution and acid resistance results for the enteric granules are shown in Table 1.

TABLE 1

| | Elution time (min) | Hardness (kp) | Disintegration time (min) | Acid resistance (%) | Abrasiveness (no.) |
|---|---|---|---|---|---|
| Enteric | | | | | |
| granules (Example 1) | 24 | — | — | 0.7 | — |
| Example 1 | 25 | 3.7 | 1.5 | 2.1 | 3 |
| Example 2 | 25 | 6.2 | 1.2 | 1.8 | 0 |
| Comparative Example 1 | 35 | 4.0 | 7.0 | 15.7 | 4 |

A centrifugal fluid coating granulator was used to coat 500 g enteric granules with 85 g of lactose while nebulizing 50 ml of a 3% aqueous solution of HPC-L, and this was followed by drying to prepare overcoated granules 1. After mixing 80 parts of the overcoated granules 1, 14 parts of dried aluminum hydroxide gel (product of Kyowa Chemical Indust., KK.), 3 parts of croscarmellose sodium (product of Asahi Chem. Indust., KK.) and 3 parts talc, a rotary tabletting machine (Model S-15, product of Kikusui Works, KK.) was used for compression at a tabletting pressure of 400 kg/cm² to prepare 7.5 mmø 180 mg tablets.

EXAMPLE 2

The tablets of Example 1 were further dried at 60° C. for 2 hours. The results for the elution time (T75%: min), hardness (Kp), disintegration time (min), acid resistance (%) and abrasiveness (no.) for Examples 1 and 2 are shown in Table 1.

Although the enteric granules of Example 1 shown in Table 1 had inferior acid resistance upon tabletting, the difference was minimal. Also, no changes were seen in the 75% elution time.

A comparison of Examples 1 and 2 reveals that drying of the enteric granule-containing tablets resulted in increased hardness and better results in the abrasiveness test.

A comparison of Comparative Example 1 and Example 1 shows that Example 1 was vastly superior, having a greater elution rate and hardness, a shorter disintegration time, and better results in the abrasiveness test. In addition, as shown in FIG. 1, there were few variations in the tablet weight during tabletting, and the tablet weights were constant even with long tabletting times.

COMPARATIVE EXAMPLE 1

A mixture of 80 parts of the overcoated granules 1 of Example 1, 14 parts of crystalline cellulose, 3 parts of croscarmellose sodium and 3 parts talc was tabletted and dried according to Example 1. The results weight variation between Example 2 and Comparative Example 1 are shown in FIG. 1.

EXAMPLE 3

A mixture of 85 parts of the overcoated granules 1 of Example 1, 6 parts of dried aluminum hydroxide gel, 3 parts of synthetic hydrotalcite, 3 parts of croscarmellose sodium and 3 parts talc was tabletted and dried according to Example 1. The results for the 75% elution time, hardness, disintegration time, acid resistance and abrasiveness test for Example 3 are shown in Table 2.

EXAMPLE 4

A multifunctional tumbling fluidized bed apparatus (Model MP-01, product of Powrex, KK., hereunder referred to as "MULTIPLEX®") was used to coat 500 g Nonpareil (32-42#) (product of Freund Indust., KK.) while nebulizing 1300 g of a 3% HPC-L suspension containing a mixture of 100 g of TU-199, 50 g of dried aluminum hydroxide gel and 450 g of lactose, and this was followed by drying and sorting to obtain 1050 g crude granules (20-42#). MULTIPLEX® was used to coat the crude granules with a mixed solution of 34 parts of the acrylic polymer-based coating agent Eudragit L30D-55, 4 parts of Macrogol 6000 and 34 parts water, to 30% with respect to the crude granules, to prepare enteric granules. MULTIPLEX® was then used to coat 500 g of the enteric granules while nebulizing 175 g of a 3% HPC-L suspension containing 85 g of lactose, and this was followed by drying to prepare overcoated granules 2. The overcoated granules 2 were tabletted and dried according to Example 1. The results for the 75% elution time, hardness, disintegration time, acid resistance and abrasiveness test for Example 4 are shown in Table 2.

TABLE 2

|  | Elution time (min) | Hardness (kp) | Disintegration time (min) | Acid resistance (%) | Abrasiveness (no.) |
| --- | --- | --- | --- | --- | --- |
| Example 2 | 25 | 6.2 | 1.2 | 1.8 | 0 |
| Example 3 | 27 | 5.7 | 1.6 | 3.0 | 0 |
| Example 4 | 22 | 6.0 | 1.1 | 2.7 | 0 |

Example 1 had a granule content of 80%, while Example 3 had a granule content of 85%. MULTIPLEX® was used for Example 4, and similar physical property values were obtained.

What is claimed is:

1. Enteric granule-containing tablets prepared by tabletting: enteric granules containing an active agent, and a second ingredient comprising one or more compounds selected from the group consisting of synthetic hydrotalcite, dried aluminum hydroxide gel, aluminum hydroxide/sodium hydrogen carbonate coprecipitate, alumina hydroxide/magnesium, synthetic aluminum silicate and dihydroxyaluminumamino acetate.

2. Enteric granule-containing tablets set forth in claim 1, wherein said mixture contains the enteric granules in an amount of 75–90% by weight with respect to the total weight of the tablets.

3. Enteric granule-containing tablets set forth in claim 2, wherein said second ingredient comprises a mixture of synthetic hydrotalcite and dried aluminum hydroxide gel.

4. Enteric granule-containing tablets set forth in claim 1, wherein the enteric granules comprise first granules in an amount of 70–80% by weight with respect to the total weight of the enteric granules.

5. Enteric granule-containing tablets set forth in claim 2, wherein the enteric granules comprise first granules in an amount of 70–80% by weight with respect to the total weight of the enteric granules.

6. Enteric granule-containing tablets set forth in claim 3, wherein the enteric granules comprise first granules in an amount of 70–80% by weight with respect to the total weight of the enteric granules.

7. Enteric granule-containing tablets set forth in claim 1, wherein the active agent is degradable in acid.

8. Enteric granule-containing tablets set forth in claim 2, wherein the active agent is degradable in acid.

9. Enteric granule-containing tablets set forth in claim 3, wherein the active agent is degradable in acid.

10. Enteric granule containing tablets set forth in claim 1, wherein the active agent is a proton pump inhibitor.

11. Enteric granule-containing tablets set forth in claim 1, wherein the active agent comprises 5-methoxy-2-[[(4-methoxy-3, 5-dimethyl-2-pyridyl)methyl]sulfinyl]imidazo[4,5-b]pyridine.

12. Enteric granule-containing tablets set forth in claim 2, wherein the active agent comprises 5-methoxy-2-[[(4-methoxy-3, 5-dimethyl-2-pyridyl)methyl]sulfinyl]imidazo[4,5-b]pyridine.

13. Enteric granule-containing tablets set forth in claim 3, wherein the active agent comprises 5-methoxy-2-[[(4-methoxy-3, 5-dimethyl-2-pyridyl)methyl]sulfinyl]imidazo[4,5-b]pyridine.

14. A method of making enteric granule-containing tablets comprising the steps of: providing enteric granules containing an active agent, and tabletting a mixture of the enteric granules and a second ingredient comprising one or more compounds selected from the group consisting of synthetic hydrotalcite, dried aluminum hydroxide gel, aluminum hydroxide/sodium hydrogen carbonate coprecipitate, alumina hydroxide/magnesium, synthetic aluminum silicate and dihydroxyaluminumamino acetate.

15. A method according to claim 14, wherein said mixture contains enteric granules in an amount of 75–90% by weight with respect to the total weight of the tablets.

16. A method according to claim 14, wherein said second ingredient comprises a mixture of synthetic hydrotalcite and dried aluminum hydroxide gel.

* * * * *